United States Patent [19]

Braun et al.

[11] 4,000,972
[45] Jan. 4, 1977

[54] MEASURING SYSTEM FOR THE PHARMACOLOGICAL MANIPULATION OF THE COAGULATION MECHANISM IN BLOOD AND FOR THE ELAPSED COAGULATION TIME

[75] Inventors: Walter Jacob Braun; John Henry Altshuler, both of Englewood; Gerald Lance Schlatter; Robert LeRoy Poland, both of Boulder, all of Colo.

[73] Assignee: Hemotec, Inc., Englewood, Colo.

[22] Filed: Jan. 16, 1976

[21] Appl. No.: 649,648

[52] U.S. Cl. .............................. 23/230 B; 73/64.1; 356/39
[51] Int. Cl.² ........................................ G01N 33/16
[58] Field of Search ............... 23/230 B; 73/64.1; 356/39, 246

[56] References Cited
UNITED STATES PATENTS

| | | | |
|---|---|---|---|
| 3,307,392 | 3/1967 | Owen et al. | 23/230 B X |
| 3,658,480 | 4/1972 | Kane et al. | 73/64.1 X |
| 3,695,842 | 10/1972 | Mintz | 73/64.1 X |
| 3,704,099 | 11/1972 | Sanz | 23/230 B X |
| 3,854,324 | 12/1974 | Altshuler et al. | 23/230 B X |

*Primary Examiner*—Robert M. Reese

[57] ABSTRACT

A system for determining the coagulation time of blood and components thereof, the amount of anticoagulant to be injected before and during surgery, and the amount of additive required to neutralize the anticoagulated blood during and after surgery. With collected samples of anticoagulated blood inserted into the system coagulation of the blood is accelerated through the controlled injection of a neutralizing additive by a corresponding injection of regulated gas. Failsafe means determine if gas is being injected into the sample and detection means detect the event of coagulation and indicate the elapsed time for coagulation. Before surgery, an anticoagulant is added to the patient's blood in a quantity necessary to avoid coagulation during surgery. The system responsive to the parameters of the patient's sex, height, and weight and/or pump volume and blood volume determines the amount of anticoagulant to be injected. During operation, samples of blood are periodically taken and analyzed to determine additional amounts of anticoagulant or neutralizing additive to inject. To neutralize the anticoagulant by the injection of a suitable additive immediately after surgery, the system determines the strength of the anticoagulant and calculates the amount of additive to be injected. To prevent the possibility of internal bleeding due to a rebound situation after surgery, additional samples of blood are taken and analyzed to calculate the amount of additive to be injected for neutralization.

43 Claims, 11 Drawing Figures

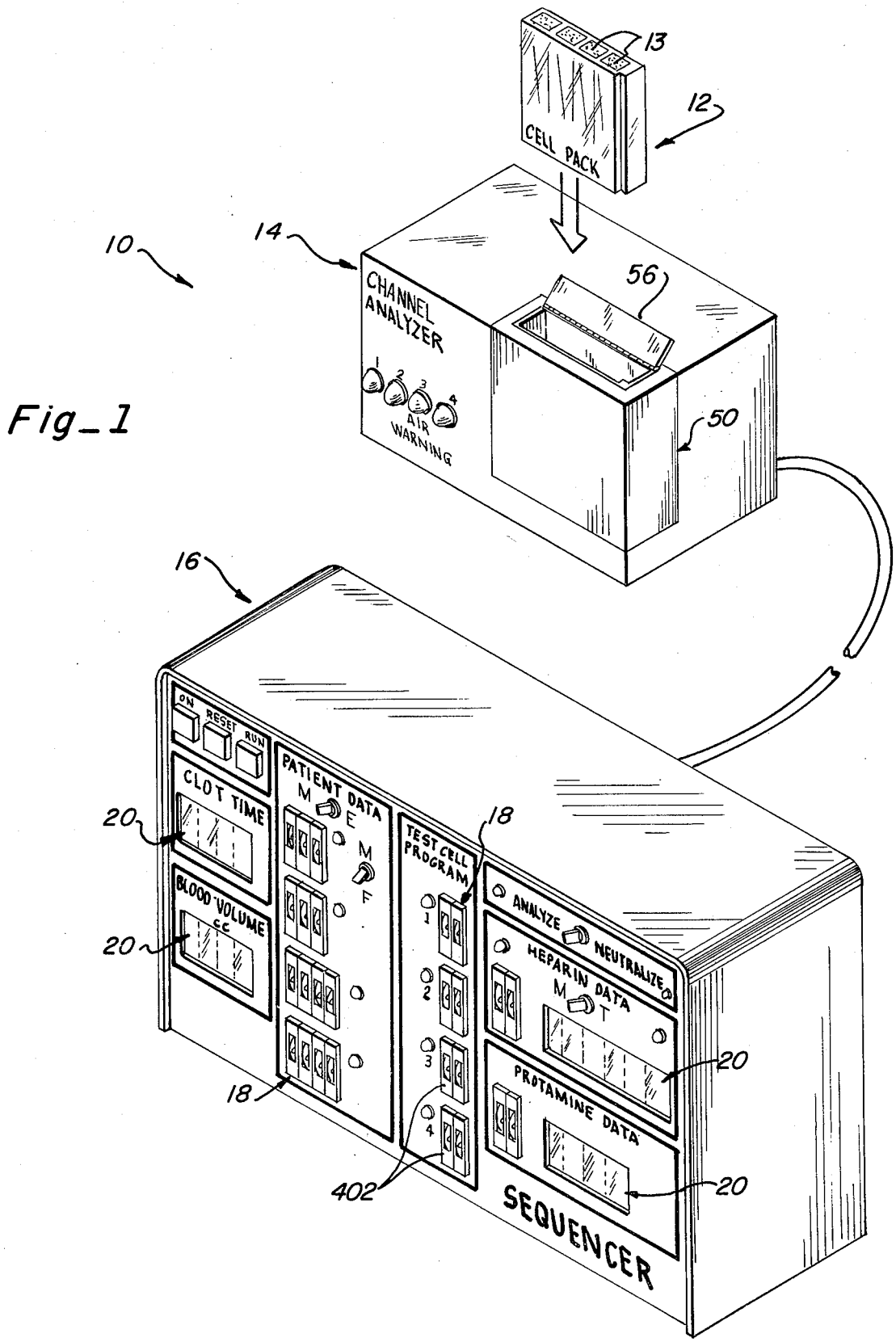
Fig_1

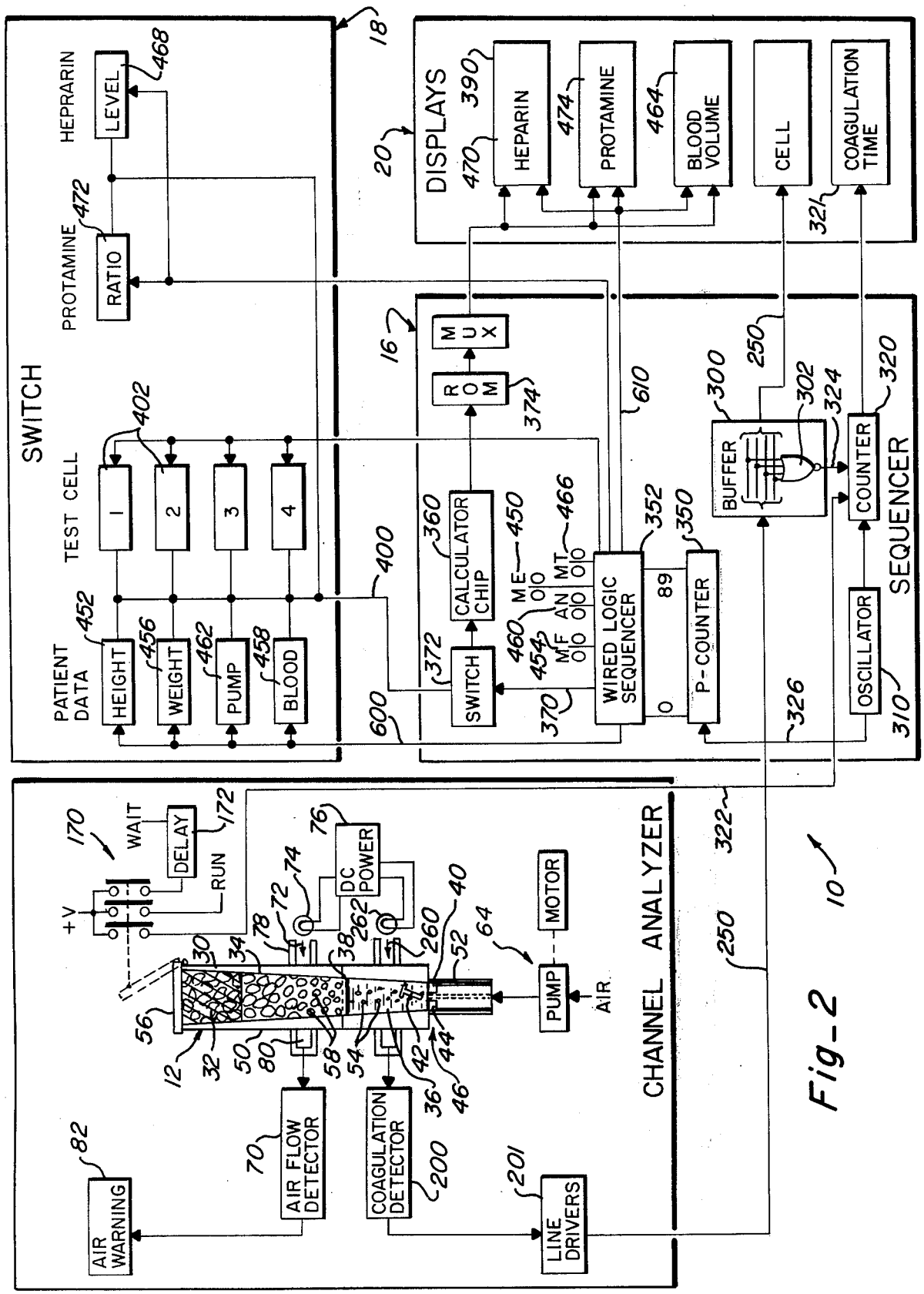
Fig_2

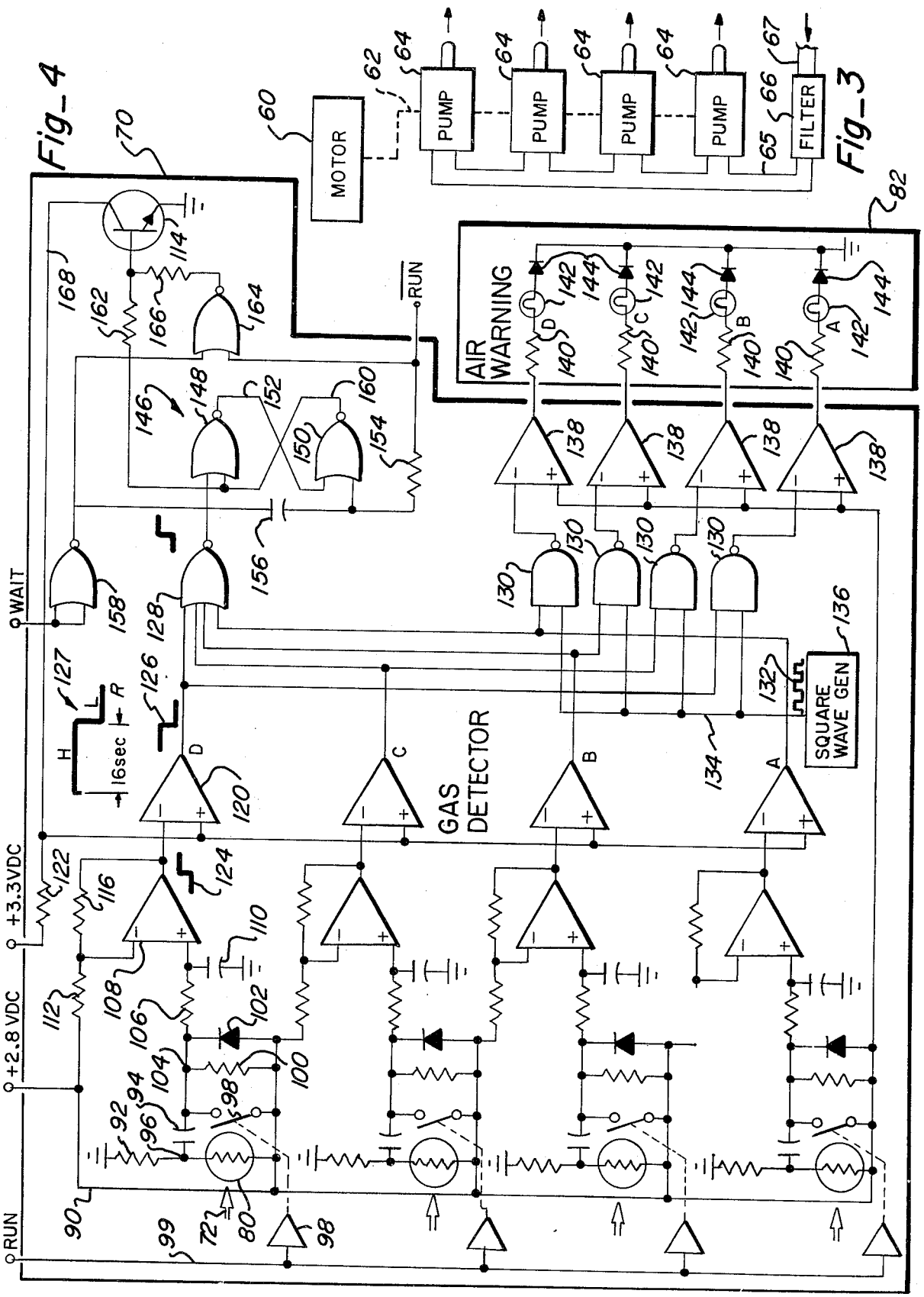

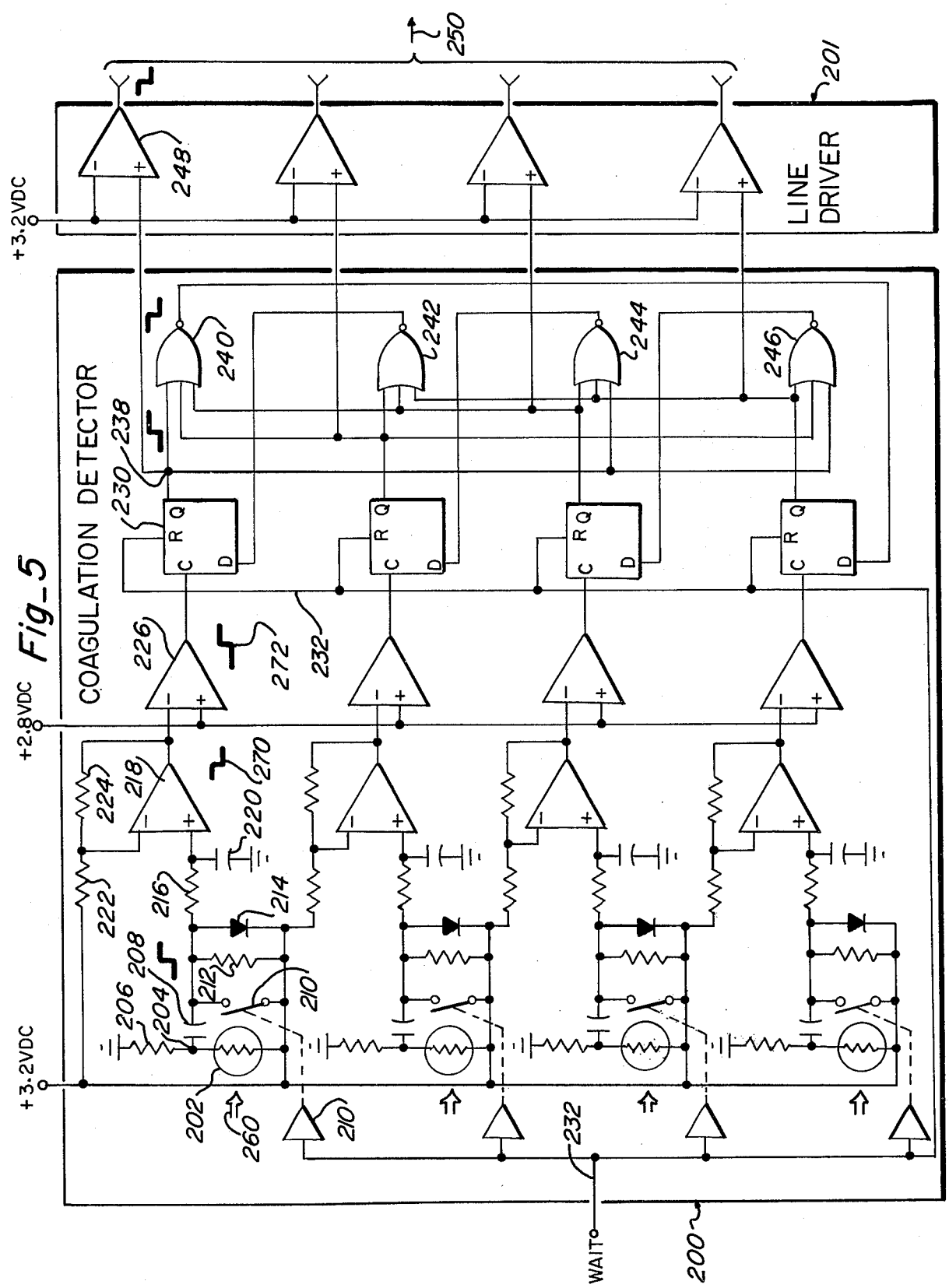
Fig_5

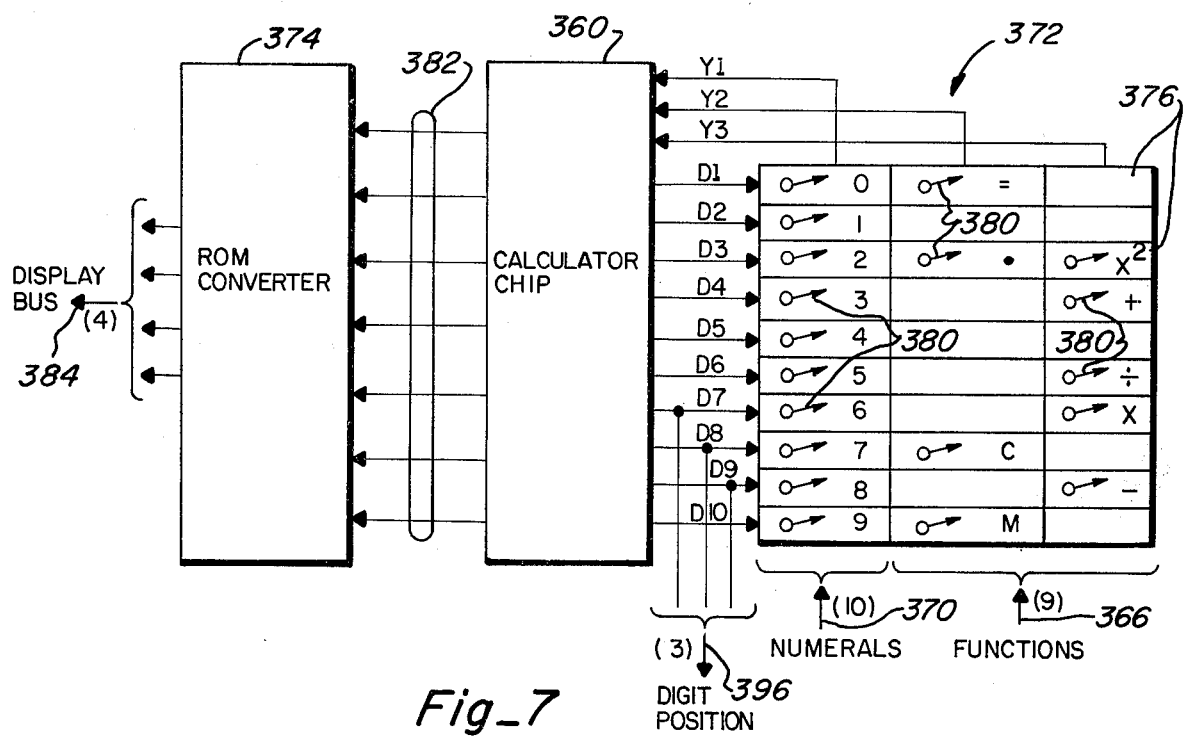
Fig_7
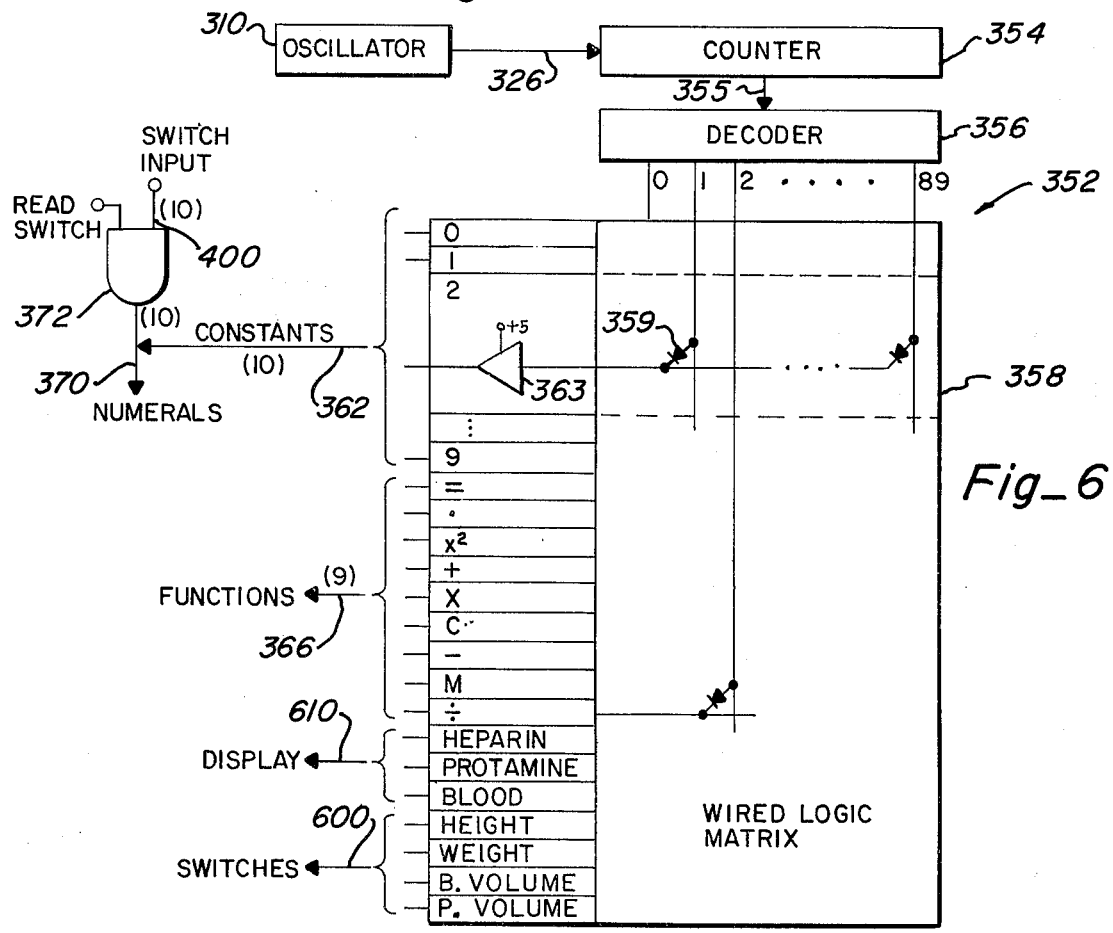
Fig_6

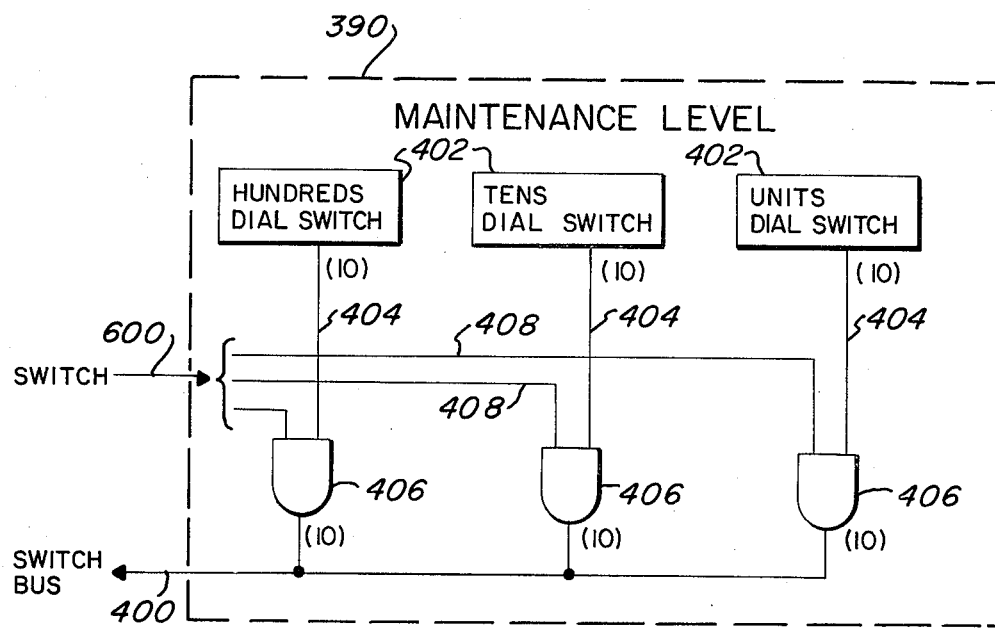
Fig_9
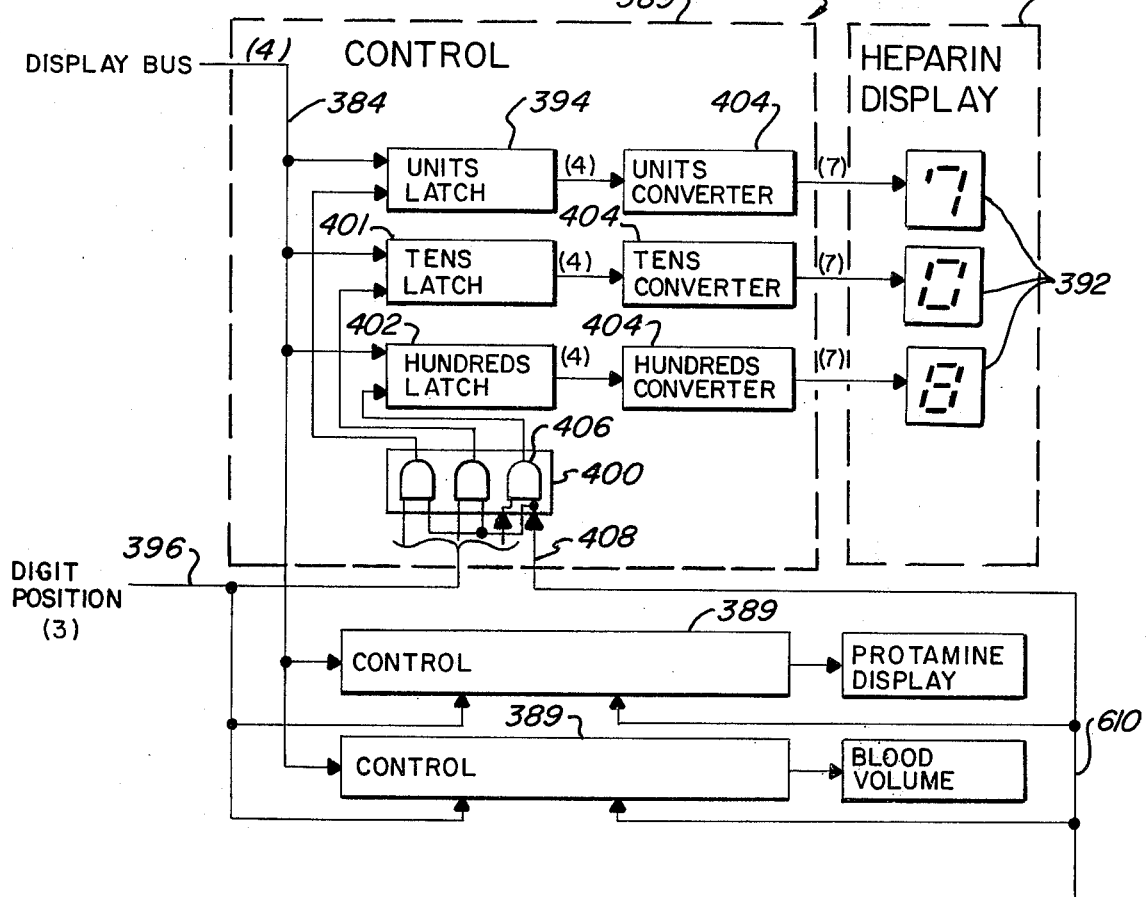
Fig_8

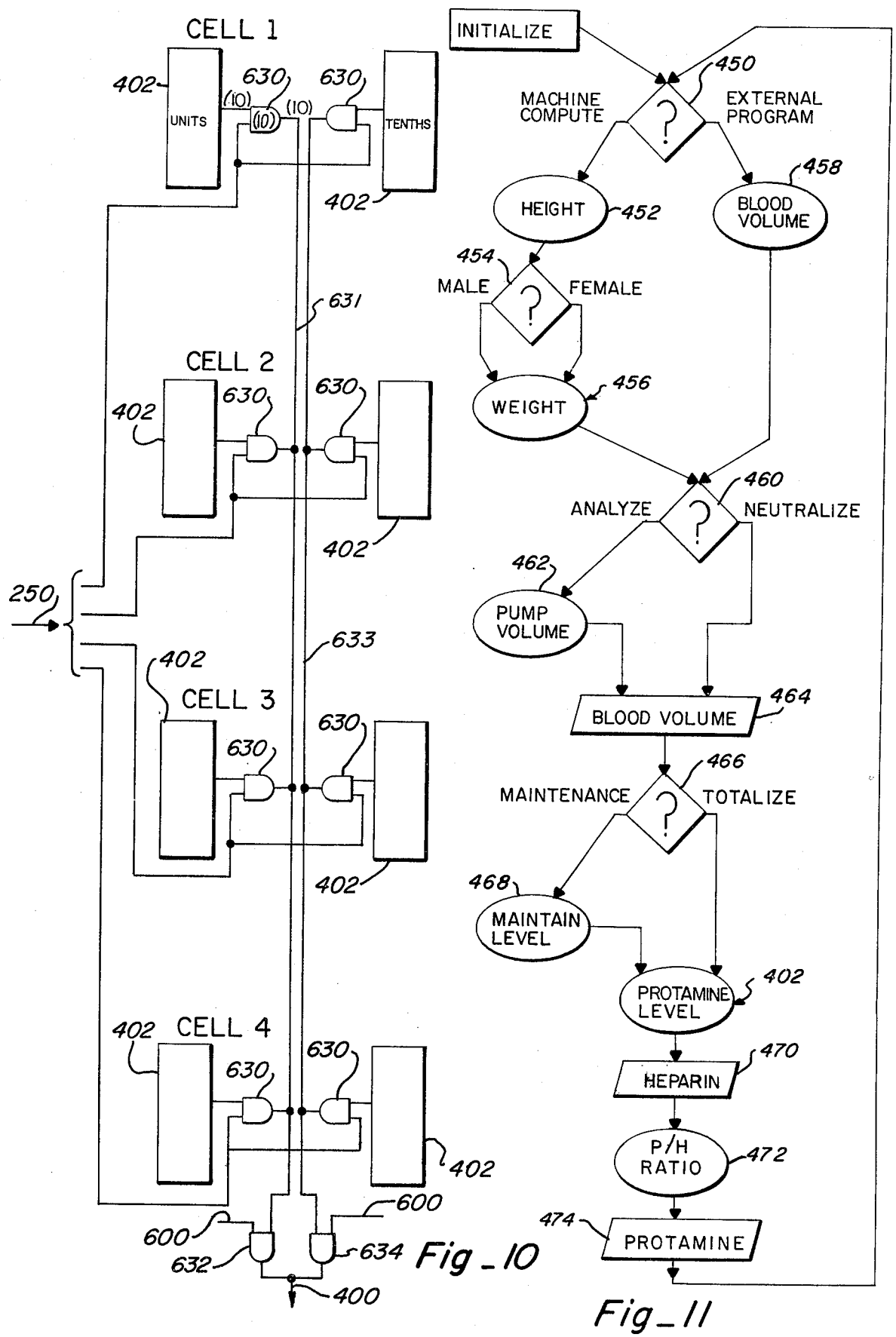
Fig_10    Fig_11

MEASURING SYSTEM FOR THE PHARMACOLOGICAL MANIPULATION OF THE COAGULATION MECHANISM IN BLOOD AND FOR THE ELAPSED COAGULATION TIME

BACKGROUND OF THE INVENTION

1. Field of the Invention

The present invention relates generally to a system for measuring blood coagulation time.

The present invention relates more particularly to a system for measuring blood coagulation time and the pharmacological manipulation of the coagulation mechanism in blood.

2. Description of the Prior Art

Lengthy surgical procedures, especially those requiring temporary cardiopulmonary bypasses and total body perfusion, involve blood coming into contact with many foreign surfaces, thereby necessitating pharmacological manipulation of the coagulation mechanism to prevent coagulation of the blood and its resultant catastrophic effects. It is known in the art of perfusion, that blood coagulation is a hemostatic process wherein certain factors normally passive in the blood-stream are stimulated into an active form which trigger a chemical chain of events resulting in a blood clot. A blood clot comprises a mass of fibrin threads surrounding entrapped cells. The process of coagulation is not completely understood, but it is well known in the art that coagulation occurs when blood is removed from the body and passed, for example, through an extracorporeal circuit.

In order to prevent coagulation during an extracorporeal bypass, various drugs may be injected into the blood. For example, sodium heparin is usually injected into patients requiring open heart surgery in order to neutralize the clotting factors. Open-heart surgery exposes blood to numerous procoagulant stimuli and requires significantly more heparin than other surgical procedures to achieve anticoagulation. Since, heparin is metabolized rapidly it has a half life of one to two hours, and injections of heparin must be continuously made during surgery. Too little heparin will cause the diastrous effect of coagulation while too much heparin will cause an equally diastrous effect of postoperative internal bleeding or hemorrhaging. The use of heparin and its half-life characteristics are well known in the art as found, for example, in Wright, et al, "Heparin Levels During and After Hypothermic Perfusion", 5 T. Card. Surg. 244–250 (1964).

A properly heparinized patient, therefore, has a concentration of heparin in his blood that is sufficient to prevent coagulation of blood but not great enough to cause internal bleeding. A surgeon, after acquiring experience, develops an insight for the amounts of heparin to use and when to inject additional heparin based on such parameters as height, weight, sex and blood volume of the patient. Obviously, such an approach involves a high degree of risk taking by the patient.

After surgery is completed it becomes necessary to neutralize the heparin to prevent postoperative internal bleeding by the injection of an appropriate additive such as protamine sulfate. If administered alone, protamine is an anticoagulant. However, when given in the presence of heparin, a stable and physiologically inert salt is formed, thus neutralizing the anticoagulant activity of both drugs. Accurate determination of the amount of protamine for neutralization is required since too little or too much protamine results in anticoagulated blood and possible postoperative bleeding. The use of protamine as a postoperative neutralizer is well known in the art; see, for example, Reed and Clark, Cardiopulmonary Perfusion (1975), Library of Congress Catalog Card Number 75–7168. After the patient is neutralized a "heparin rebound" condition may arise in which the patient's blood becomes heparinized due to a reappearance of heparin. Although heparin rebound is not fully understood, it is well known in the art, see Ellison, et al, "Heparin Rebound", 67 J. Thoracic Card. Surg. 723–729 (1974).

Heparin is commercially provided in varying concentrations depending on its potency from a variety of sources such as beef lung, beef liver, beef mucosa, and pork mucosa. Protamine is also commercially available in a variety of concentrations also emanating from a variety of sources such as the sperm of salmon and certain other fish.

The classical method of determining blood coagulation time is to determine the Lee-White clotting time. A sample of blood is inserted into a centrifuge in order to separate the serum from the blood. The serum is then inserted into a testing machine which determines the coagulation time by detecting a change in the opaqueness of the serum. The Lee-White process is a long process generally taking thirty minutes or longer and which involves excessive manual handling on foreign surfaces of the blood and the use of a centrifuge and a separate testing machine. The Lee-White method is not practical for determining clotting time parameters of anticoagulated blood during surgery.

A conventional approach for determining the amount of protamine at the conclusion of a heart-lung extracorporeal bypass is the protamine titration method as disclosed, for example, in Hurt, et al, "The Neutralization of Heparin by Protamine in Extracorporeal Circulation", 32 J. Thoracic Card. Surg. 612–619 (1956). The protamine titration method is a developed laboratory skill and involves using test tubes, known titration techniques, and visually determining the event of coagulation. The titration normally takes 15–20 minutes and is a function of the lab technician's skill.

Another conventional prior art approach uses a test tube sample of the heparinized blood in which is manually injected via a hypodermic needle a known amount of protamine. A gas is injected into the test tube mixture to accelerate coagulation, the gas acts as a foreign body which stimulates the clotting factors. When the blood coagulates a back pressure is delivered into the gas delivery system which is sensed by a pressure detector. The above approach is disclosed in Altshuler, et al, "Hemotensiometry", 18 Annals of Thoracic Surg. 516–530 (1974).

The above prior art approaches are generally primarily dependent on operator skill, and are, therefore, highly nonreproducible. In addition, the prior art approaches are slow in measuring the event of coagulation. At the conclusion of surgery involving an extracorporeal bypass, hemorrage-related morbidity and mortality poses a constant threat to the heparinized patient. Although protamine and other additives effectively neutralize heparin, an overdose of protamine may cause internal bleeding, shock or thrombocytopenia. A patient who is rapidly neutralized after disconnecting the bypass and during the rebound stage will be in a minimum risk condition. If post operative hemorrhaging then occurs, the cause in abnormal and generally mechanical thereby requiring further re-exploration. None of the above prior art approaches provide an apparatus that rapidly measures coagulation time of blood prior to surgery, that rapidly determines the amount of heparin to inject into a patient's blood prior to surgery, that rapidly measures the heparin strength in the blood during surgery, and that rapidly measures the amount of protamine necessary for neutralizing of heparin after surgery and during rebound. Finally, none of the prior art approaches take into account the various patient parameters of height, weight, sex, blood volume and pump volume.

OBJECTS OF THE INVENTION

The present invention has for its primary object provision of a new apparatus for measuring the coagulation time of blood.

It is another object of the present invention to provide a compact, self-contained testing unit which automatically displays blood coagulation time while minimizing exposure of the blood to foreign surfaces.

It is another object of the present invention to provide a new coagulation measurement system which determines the amount of anticoagulant to be added to a patient's blood for surgical operations.

It is another object of the present invention to provide a new means of injecting gas into blood samples to accelerate coagulation thereof.

It is still another object of the present invention to provide a failsafe detection apparatus to determine whether gas bubbles are being injected into the blood.

It is still another object of the present invention to provide a new apparatus for determining the strength of anticoagulant in blood.

It is still another object of the present invention to provide a new apparatus for determining the strength of heparin in blood.

It is still another object of the present invention to provide a new apparatus for determining the amount of protamine necessary to neutralize heparinized blood.

It is still another object of the present invention to provide a new apparatus which automatically determines concentration of an anticoagulant to be added to a patient's blood based on the patient's parameters of height, weight, sex, and blood volume.

It is still a further object of the present invention to provide a novel system including holders for the blood samples, a detector operatively engaging the holders for detecting the first holder to have coagulation of the blood sample therein and a timer being activated upon the engagement of the detector and being stopped upon the detection of coagulation.

It is a further object of the present invention to provide a novel system for determining the coagulation time for anticoagulated blood after neutralizing the anticoagulant in the blood with an additive including a plurality of cells holding samples of the blood, and a corresponding plurality of detectors wherein one of said detectors being uniquely cooperative with one of said cells for sensing coagulation of the blood sample in the assigned cell, a timer being activated when the cells are in proper orientation with the detectors, and a circuit operative upon the first detector to sense coagulation of the blood for inhibiting the timer and for signalling which one of the plurality of cells has the coagulated blood sample.

SUMMARY OF THE INVENTION

The foregoing and other objects are obtained in accordance with the present invention whereby samples of blood with or without an anticoagulant, such as heparin, are collected and stored in a compact cell pack having a plurality of channels each of which contain the same amount of blood. The cell pack containing the blood sample is inserted into a channel analyzer of the present invention. Simultaneous with insertion, a neutralizing additive, such as protamine, may be automatically injected into the blood of each cell. In any event, gas bubbles are injected, as foreign objects, into the blood and additive mixture to accelerate coagulation. A detection apparatus determines when coagulation has occurred and automatically relays this information to the sequencer of the present invention. The sequencer displays the cumulative coagulation time and automatically determines the heparin concentration, if any, within the blood, the amount of anticoagulant to be injected into the blood to correct the heparin half-life loss, and the amount of additive if required, to neutralize the anticoagulant within the blood. The sequencer is designed to rapidly and reproducibly determine, visibly display, and to automatically take into account various patient parameters such as sex, height, weight, patient blood volume, and the pump volume. In addition, the system of the present invention can be used without the injection of protamine to determine whether blood has normal coagulation time or whether defects are present which result in abnormal coagulation characteristics.

The channel analyzer is uniquely designed to encourage the coagulation of blood in a plurality of separate cells each of which contains a different concentration of additive. Gas, under constant pressure, is delivered via separate and individual delivery systems into the blood of each cell in order to accelerate coagulation. Each cell of the cell pack has a corresponding channel in the channel analyzer. Each channel comprises two light sensitive detectors, the first detector determines whether or not gas is being injected into the cell and, the second detector determines whether or not the blood sample has coagulated. The first light sensitive detector activates the sequencer of the present invention for further analyzing the various parameters of the blood.

In system operation, a sample of blood is injected into each cell of the cell pack to a predetermined level. The cell pack containing the samples is inserted into the analyzer and a cover closed over the top of the cell pack to activate the system. The additive and a gas are then injected into the blood sample of each cell through individual nozzles. A build-up of liquid blood bubbles occurs in the space above the level of the sample, the bubbles rupture, and the liquid blood is released to reflux down the sides of the cell. After a time interval, the blood, due to the presence of the gas as a foreign body, commences to coagulate and take on the composition of a gel-like material. At the event of coagulation, the bubbles formed on the surface of the sample transport the gel-like blood upwardly into the gauze located in the hopper above the surface of the sample. Blood gel accumulates in the gauze located in the hopper thereby reducing the level of the sample in the bottom of the cell to a level at which light transmits into the second detector with greatly increased intensity. The rate of change in the amount of light received by the second detector increases significantly at this time and is amplified and transmitted to the sequencer.

The sequencer is uniquely designed to be activated upon the insertion of the cell pack into the channel analyzer. When the signal from the channel analyzer representing coagulation of blood in one of the cells is received, a timer stops and the coagulation time is displayed as well as which cell was the first to coagulate. An oscillator further drives a program counter which, step by step, drives a wired logic sequencer. The wired logic sequencer interrogates a plurality of switch inputs relating to patient, test cell, heparin, and protamine parameters uniquely suited for a particular patient and delivers that information into a calculator. The calculator determines the heparin and protamine levels and concentrations for the particular patient.

The present invention finds application in four modes of surgery and, further provides a fast and highly reproducible means for measuring the coagulation time of blood. Prior to surgery, it is necessary to determine the coagulation time of a patient's blood in order to determine the amount of an anticoagulant, usually heparin, to be added to the blood volume of the patient. It is further important to determine whether the patient has a normal or abnormal coagulation mechanism. It is, therefore, imperative that the amount of heparin added is not an excessive amount which may result in internal bleeding or an inadequate amount which would result in passage of blood clots into the body. The present invention determines the amount of heparin to be initially added to a patient's body based on that patient's particular body parameters. After the patient is initially heparinized, the patient's blood is sampled periodically to determine how much additional heparin is required to overcome the decay of heparin due to its half-life. After surgery, the system of the present invention finds application in determining the amount of protamine necessary to neutralize the heparin within the patient's blood. And finally, if after neutralizing, the patient under-goes heparin rebound, the system of the present invention determines the amount of protamine to be added to minimize such rebound.

Other objects, advantages and capabilities of the present invention will become more apparent as the description proceeds taken in conjunction with the accompanying drawing.

DESCRIPTION OF THE DRAWINGS

FIG. 1 is a perspective view of the present invention illustrating the cell pack, the channel analyzer, and the sequencer relationships.

FIG. 2 is a diagrammatic layout of the system of the present invention illustrating one channel of the cell pack being analyzed.

FIG. 3 is a schematic representation of the gas delivery system of the present invention.

FIG. 4 is the electronic schematic of the gas detector and corresponding warning circuits of the present invention.

FIG. 5 is the electronic schematic of the coagulation detector circuit of the present invention.

FIG. 6 is a diagrammatic representation with partial electronic schematic of the wired logic sequencer of the present invention.

FIG. 7 is a diagrammatic representation of the calculator chip and the corresponding input and output circuits of the present invention.

FIG. 8 is a diagrammatic representation of the display circuits of the present invention.

FIG. 9 is a diagrammatic representation of the switch inputs for the heparin maintenance level.

FIG. 10 is a diagrammatic representation of the protamine concentration switch inputs of the present invention.

FIG. 11 is a flow diagram depicting the sequence of operation of the present invention.

DESCRIPTION OF THE PREFERRED EMBODIMENT

The coagulation measurement system 10 of the present invention, shown in FIG. 1, comprises a cell pack 12 containing a specimen of blood and a predetermined amount of additive separated therefrom, a channel analyzer 14 responsive to the insertion of the cell pack 12 for effecting mixture of the additive with the blood and for injection of gas into the mixture to accelerate coagulation, and a sequencer 16 also responsive to the insertion of the cell pack 12 for determining the time for coagulation of the blood and for determining the amount of anticoagulant to be injected into the patient's blood. The sequencer 16 includes a plurality of switch inputs 18 for providing the sequencer 16 with a variety of patient and anticoagulant parameters, and displays 20 for displaying the time for coagulation and other parameters. As will become apparent, this invention finds particular application for determining the strength of an anticoagulant, such as heparin, injected into blood for surgery, by neutralizing the heparin in a sample of the blood with a known concentration of additive, such as protamine.

The cell pack 12 comprises a plurality of distinct cells 13 each of which is of identical design. The details of cell pack 12 are set forth in a co-pending application Ser. No. 649,649 entitled "Apparatus and Method for the Pharmacological Manipulation of the Coagulation Mechanism in Blood and for Signalling the Event of Blood Coagulation", filed on Jan. 16, 1976 and that disclosure is specifically incorporated by reference into this specification. Briefly summarized, each cell pack 12, as shown in FIG. 2 includes an upper cavity or hopper area 30 containing a gauze 32, a vial 34 for holding blood 36 filled to a predetermined level 38, a chamber 40 for holding the additive, said chamber being separated from the vial 34 by a break away cap 42, and a slideable plug 44 defining the lower portion of the chamber 40. Each cell 13 stores a predetermined amount of additive 46 in the chamber 40. When the cell pack 12 is inserted into the holder 50 of the analyzer 14 of the present invention, a protruding air nozzle 52 causes the cap 42 to break away, moves the slideable plug 44 upwardly thereby injecting the additive into the blood 36, and finally injects a constant stream of gas 54 into the blood. A conventional mechanical latch 56 locks the cell pack 12 firmly into holder 50 so that the nozzle 52 forms a gas-tight seal with plug 44 thereby ensuring constant delivery of the gas bubbles 54 into the blood.

In this manner, gas bubbles 54 are injected as a foreign body into the blood 36 thereby accelerating coagulation by effectuating two distinct sequential phases. The first phase, termed "liquid-bubble" is generated as the gas is injected into the blood specimen 36 and bubbles 58 transporting some of the blood are formed above the surface of the blood The liquid-bubble phase forms above the blood specimen after a period of time has elapsed for gas injection. The liquid-bubbles 58 abut the tapered sides of the vial 34 and the undersurface of the gauze 32 and burst to allow the transported liquid blood to reflux downwardly along the tapered sides. The second phase, termed "gel-bubble", occurs when the blood commences to coagulate. In this phase, the blood becomes gel-like and the transported gel-like blood in the bubbles becomes trapped in the gauze 32. At the event of coagulation, no refluxing of the blood occurs and the level of the specimen blood 36 drops rapidly due to the collection of the transported coagulated blood by the gauze 32.

The gas delivery system is schematically shown in FIG. 3 to comprise a conventional motor 60 interconnected via a mechanical shaft 62 to a plurality of four separate pumps or compressor 64 so that each pump 64 is driven at the same speed as the others. Each pump 64 is conventional of the type manufactured by Barnet Corp., Barrington, Illinois, Model 7017-70. Each pump 64 receives gas via a delivery conduit 65 from a common filter 66 which has access 67 to a gas source, not shown. The gas that is delivered from the pump 64 is delivered at a constant rate into the nozzle 52 and is identical to the rate of gas being delivered from each of the other pumps 64. Each pump 64 is adjustable in a conventional fashion, adjustment may be made to any one pump to ensure constant delivery.

It is to be understood that the aforesaid reference co-pending application discloses only a preferable device for signalling coagulation of blood and components thereof. Other devices signalling coagulation of blood and components thereof may also be used by the system of the present invention.

A gas flow detector circuit 70 is shown in FIG. 2 for the channel analyzer 14. A beam of light 72 is generated from light source 74 which is powered by a conventional DC power source 76. The light beam 72 is directed by a light guide 78 attached to the holder 50 and into the vial 34 at a point above the predetermined fill level 38 of the blood 36. When liquid or gel-bubbles 58 exist in the vial 34, the optical signal 72 is attenuated and the photocell 80 detects only a background ambient of light. In the event that no liquid or gel-bubbles 58 are formed, then the light beam 72 impinges directly on the photocell 80 and the gas detection circuit 70 operates a gas warning circuit 82.

The details of the gas detection and warning circuits, 70 and 82, are shown in FIG. 4. The light beam 72 is detected by the photocell 80 of which one end is connected to a positive 2.8 volt DC potential over lead 90 and the other end of which is connected through a resistor 92 to ground and an AC coupling capacitor 94, both at node 96. The photocell 80 is shunted by a solid state switch 98 until the RUN signal appears on lead 99. The solid state switch 98 is conventional and of the type manufactured by National Semi-conductor as CMOS 4016. A resistor 100 and diode 102 parallel combination is further in parallel with the series connection of the coupling capacitor and the photocell 80.

The node 104 between the coupling capacitor 94 and the resistor 100 and diode 102 parallel combination is further connected through a resistor 106 to the PLUS input of an operational amplifier 108 and through a capacitor 110 to ground. The MINUS input of the operational amplifier 108 is fixedly biased at a predetermined value through a resistor 112 to the 2.8 volt DC source. The operational amplifier 108 is conventional and is of the type manufactured by National Semiconductor as Model LM324.

The output from the operational amplifier 108 is fed back through a resistor 116 to the MINUS input. The relationship of resistor 116 to resistor 112 determines the gain of the amplifier 108. The output of the operational amplifier 108 further activates a second operational amplifier 120 at the MINUS input. The PLUS input of the second operational amplifier 120 is connected through a resistor 122 to a 3.3 volt DC source and through the collector of transistor 114 to ground. The second operational amplifier 120 is provided to amplify the gain of the signal, as shown in wave 124, from the first operational amplifier 108, as shown by wave 126.

Each channel of the channel analyzer 14 has a detector stage for each cell identical to that presented above. In FIG. 4, four stages having outputs at A, B, C, and D are shown. Each output of the second operational amplifier 120 from each channel collectively enters a NOR-GATE 128 and individually accesses a plurality of NAND-GATES 130. Each NAND-GATE 130 is continually activated on the remaining input by the square wave binary pulse 132 appearing on lead 134 from a conventional square wave generator 136. The output of each NAND-GATE 130 is connected to the MINUS input of a corresponding operational amplifier 138. The PLUS input of the operational amplifier 138 is connected over lead 90 to the 2.8 volt DC source. The operational amplifier 138 amplifies the binary signal from the corresponding NAND-GATE 130 and delivers the amplified signal through a bias resistor 140 and to a warning lamp 142 that is protected by a diode 144 through to ground.

The output of the NOR-GATE 128 is delivered to a NOR-GATE flip-flop 146 comprised of NOR-GATES 148 and 150 interconnected conventionally. The output of NOR-GATE 148 is connected over lead 152 to one input of NOR-GATE 150. The other input to NOR-GATE 150 is DC-coupled through resistor 154 to the $\overline{\text{RUN}}$ control signal and further is AC-coupled through capacitor 156 to the ouptu of NOR-GATE 158. The output of NOR-GATE 150 is delivered over lead 160 to one input of NOR-GATE 148 output is further delivered through resistor 162 to the base of transistor 114. A WAIT signal is applied to NOR-GATE 158, inverted and delivered to a first input of NOR-GATE 164, the second input of which is connected to $\overline{\text{RUN}}$. The output of NOR-GATE 164 is delivered through resistor 166 to the base of transistor 114. Transistor 114 is a conventional transistor such as preferably Model No. 2N3568. The emitter of transistor 114 is connected to ground and the collector is connected over lead 168 to the PLUS inputs of operational amplifiers 120. The following are typical values of the components utilized for the above-described circuit:

| | | | | |
|---|---|---|---|---|
| Resistor 92 | = | 10 K ohms | Resistor 116 | = 100 K ohms |
| Capacitor 94 | = | 10 mf | Resistor 154 | = .1 M ohm |
| Resistor 100 | = | 1 M ohms | Capacitor 156 | = 1 mf |
| Resistor 106 | = | 100 K ohms | Resistor 162 | = 10 K ohms |
| Capacitor 110 | = | 10 mf | Resistor 166 | = 10 K ohms |
| Resistor 112 | = | 47 K ohms | | |

In operation, the air detector circuit 70 of FIG. 4 performs in the following manner. When the cell pack 12 is inserted into the channel analyzer 14, gas is delivered upwardly through the blood 36 to effectuate the formation of liquid bubbles 58 in the space above the level of the blood. The RUN and WAIT signal immediately go high, as shown in FIG. 2, by the activation of switch 170. The WAIT signal, however, goes low after a 16 second delay due to the series interconnection of a conventional delay circuit 172. The high on the RUN lead 99 activates the solid state switch 98 to open thereby removing the shunt and permitting photocell 80 to respond to incoming light signals 72. The simultaneous high on the WAIT control lead effects a corresponding low at the output of NOR-GATE 158 which accesses the first input of NOR-GATE 164 the second input of which is also low due to the low condition of $\overline{\text{RUN}}$. Two simultaneous lows on NOR-GATE 164 cause the output to go high. At the same time, the flip-flop 146 is reset by application of the low $\overline{\text{RUN}}$ signal so that the output of NOR-GATE 150 goes high which is delivered through resistor 162 to the base of transistor 114. Both inputs to the base of transistor 114 are now high turning the transistor 114 "ON" which thereby delivers a low signal over lead 168 to turn the amplifiers 120 "OFF" so that their corresponding outputs are held low. The operational amplifiers 120 are used in the conventional and well-known comparator mode and any signals appearing on the MINUS input will not be extended to the output when the PLUS input is held low. The outputs of the four amplifiers 120 are, therefore, low and are delivered collectively to the corresponding four inputs of NOR-GATE thereby effecting the output of which to go high. At this time both inputs to NOR-GATE 148 are high and the flip-flop 146 is latched so that the output of gate 150 on lead 160 will be held high.

After 16 seconds have elapsed, the delay circuit 172 causes the WAIT signal to go low, as shown in wave 127, thereby effecting a high signal at the output of NOR-GATE 158 which is delivered to one input of the NOR-GATE 164 causing the output to go low. Simultaneously the high signal from the output of gate 158 is delivered through the AC-coupling capacitor 156 to reset the flip-flop 146 causing the output of NOR-GATE 150 to go low which is delivered over lead 160 through resistor 162 to the base of transistor 116. At this time both inputs on the base of transistor 116 are low causing the transistor 114 to turn OFF. The OFF-state of transistor 114 is delivered over lead 168 as a high signal to the PLUS inputs of amplifiers 120. At this time the status of the gas flow in each cell will be extended to the output of amplifier 120 as follows. If gas is flowing through the blood 36 in the vial 34 of cell 13, then the light 72 will be attenuated and photocell 80 will be maintained in a high resistive state, the signal at the output of amplifier 108 will be held low. On the other hand, if no gas is flowing, the light 72 causes the photocell to have a low resistivity which, in turn, effects a high output for amplifier 108.

When the PLUS inputs of amplifiers 120 go high as previously discussed and if the gas flow status of all cells is proper, the outputs of all amplifiers 120 remain low. Therefore, the output of gate 128 is maintained high and flip-flop 146 remains with a high on lead 160 since the transient high pulse created by the transition of WAIT from a high to a low and delivered through the AC-coupling capacitor 156 returns to a low value. The flip-flop 146 remains latched to effectuate a low condition to the PLUS inputs of amplifier 120.

If, however, one or more cells has defective air flow, then the output of amplifier 120 becomes high during the sampling interval when the transistor 114 is "OFF" as previously discussed. The output of gate 128 now becomes low. At this time, the two inputs of NOR-GATE 148 are low forcing the output 152 high. The flip-flop now latches with the output of NOR-GATE 150 being low on lead 160. The transistor 116 is now latched in the OFF state to continually deliver a high to the PLUS inputs of amplifiers 120. The high output of the amplifier 120 corresponding to the cell having no gas is delivered to the corresponding NAND-GATE 130 to effectuate flashing of the corresponding lamp 142.

In summary, the gas detector circuit 70 is nonresponsive for 16 seconds during a WAIT interval. When the WAIT interval ends a sampling pulse is generated through the AC coupling capacitor 156. If air flow in all channels is proper, then during the sampling time interval flip-flop 146 remains latched to maintain transistor 114 in the "ON" state even after the sampling pulse goes away. If, however, one or more channels indicates defective flow, the sampling pulse latches in the opposite condition with transistor 114 in the "OFF" state and an appropriate lamp 142 is flashed. It is to be understood that the above description is of a preferable embodiment and that other conventional gas flow detectors may likewise find application in the system of the present invention for the detection of gas flow whether electronic or mechanical.

The coagulation detector 200, shown in FIG. 5, includes a photodetector 202 biased to a 3.2 volt DC source at one end and the other end of which is connected to a node 204 to which is connected a resistor 206 connected to ground. An AC-coupling capacitor 208 is also connected to the node 204 and the other end of which is connected to a solid-state switch 210 which is connected directly to the 3.2 volt DC source. The solid-state switch 210 is controlled by the WAIT signal on lead 232. Connected in parallel with the coupling capacitor 208 and the photodetector 202 series combination is the parallel combination of resistor 212 and diode 214. The coupling capacitor 208 is further connected through a resistor 216 to the PLUS input of an operational amplifier 218. The PLUS input of the operational amplifier 218 is further connected to ground through capacitor 220. The MINUS input of the operational amplifier 218 is biased through a resistor 222 to the 3.2 volt DC source. The output of the operational amplifier 218 is connected through a resistor 224 back to the MINUS input of the operational 1 amplifier 218. The output of the operational amplifier 218 is further connected to the MINUS input of a second operational amplifier 226, the PLUS input of which is connected to a 2.8 volt DC source. The output of the second operational amplifier 226 is connected to the clock input C of a conventional D-flip-flop circuit 230 preferable of the type known as CMOS 4013 made by National Semiconductor. The reset input R of each D-flip-flop 230 is connected to the WAIT signal over lead 232. The Q output on lead 238 interconnects with NOR-GATE 240, 242, 244, and 246 and with the PLUS input of the operational amplifier 248. The output of the amplifier 248 is delivered over the bus 250 to the sequencer 16. The outputs of each NOR-GATE 240, 242, 244 and 246 access the D input of the next succeeding D-flip-flop 230.

The operation of the coagulation detector 200 occurs in the following manner. Upon closing of the cover 56 over the cell pack 12, switches 170 close to provide a high to the delay circuit 172 which outputs a high on lead 232 for 16 seconds and which then becomes low. The transition to a low value opens the solid-state switch 210, as shown in FIG. 5, to remove the shunt and to permit the photocell 202 to operate the amplifier 218. Initially, the light 260 from source 262 is greatly attentuated due to the presence of blood 36 and the photocell 202 stays in a high resistive state. However, when the blood level drops due to coagulation, as previously discussed due to collection of the blood by the gauze, the light 260 impinges on photocell 202 causing it to reduce resistivity. The potential at node 204 thereby correspondingly increases. The rate of change of potential at node 204 is amplified by amplifier 218 into a high-to-low transition that is converted into a low-to-high transition by amplifier 226, as shown by waves 270 and 272 respectively. The low-to-high transition, wave 272, effectuates the transfer of information at the D input to the Q output of flip-flop 230. It is to be noted, that each flip-flop 230 was initially reset by the high-to-low transition on lead 232 by the WAIT signal at the end of the 16 second period to provide a low Q output. Since low Q outputs collectively access the plurality of NOR-GATES 240, 242, 244, and 246, the outputs of each will be held high. Therefore, all D inputs are high so that when the C input is clocked, as previously mentioned, Q becomes high. With Q high, amplifier 248 extends this signal to the sequencer 16 over bus 250. The high value on Q further effectuates a low on the D inputs to the remaining D-flip-flops 230 through NOR-GATES 240, 244, and 246 thereby inhibiting the other channels from signalling the sequencer 16. The following lists typical values of the components found in the coagulation detector 200:

| resistor 206 | = | 10 K ohms | capacitor 208 | = | 10 mf |
| resistor 212 | = | 1 M ohm | resistor 216 | = | 100 K ohm |
| resistor 220 | = | 10 mf | resistor 222 | = | 47 K ohm |
| resistor 224 | = | 100 K ohm | | | |

The coagulation detector circuit 200, shown in FIG. 5, is the preferable embodiment. Other conventional detectors whether electronic or mechanical which signal the first of a plurality of cells containing blood to coagulate may be utilized by the system of the present invention.

Referring now to FIG. 2, the bus 250 from the cell analyzer 14 delivers information, indicative of which one of four cells has coagulated first, into a buffer 300 of the sequencer 16. The buffer 300 comprises a NOR-GATE 302 having as inputs the four leads of bus 250. A conventional oscillator 310 and multistage divider of the type preferably manufactured by MOSTEK as Model 5009P may be used to drive the binary counter 320 with a plurality of binary pulses at, for example, a one KHz rate. The binary counter 320 commences to count the pulses from the oscillator 310 when the cell pack 12 is inserted into the cell analyzer 14 and switch 170 is closed to provide an activation signal over lead 322. The counter 320 is inhibited from counting pulses from the oscillator 310 when a coagulation signal appears on bus 250. As mentioned, the coagulation signal is high and thereby causing gate 302 to extend a low signal to inhibit the counter 320 over lead 324 in the event that any one cell coagulates. The output of the counter 320 is decoded and converted into signals necessary to drive a conventional numerical display 321. It is to be understood that the use of an oscillator 310 to drive a binary counter 320 which is under control of appropriate start and inhibit signals for displaying time passage is well understood in the art and is conventional in its approach. Therefore, while the above approach is preferable any of a number of conventional timing and display arrangements may be utilized in the system of the present invention for displaying the elapsed coagulation time for the first of a plurality of cells to coagulate.

The oscillator 310 further drives a program counter 350 which in turn controls a wired logic sequencer 352. As will become evident in the ensuing discussion, the wired logic sequencer 352 controls the remaining system of the present invention. FIG. 6 shows the details of the wired logic sequencer 352 to include the oscillator 310 driving the program counter 354 over lead 326. The program counter 354 may be any conventional binary counter. The output of the binary counter 354 accesses a conventional binary decoder 356 over bus 355, the output of which contains ninety discrete signal leads. The use of a binary counter 354 driven by an oscillator 310 and driving a decoder 356 is well known in the art. Through interaction of the oscillator 310 with the counter 354, the output of the decoder 356 is sequentially stepped with a pulse first appearing on the 0 lead, with the next sequential pulse appearing on the 1 lead and so forth until each output lead of the decoder is sequentially stepped with the pulse. After the pulse appears on lead 89, then the next pulse would appear on lead 0 and the entire sequence would be repeated. The cycle time for the control pulse to originate from and return to the 0 lead is preferably three seconds in the present embodiment.

The decoder 356 directly accesses the wired logic matrix 358 which is essentially a conventional matrix network. The wired logic matrix 358 interacts with a calculator chip 360 in a manner which will be more fully described. Suffice it to say that certain output leads of the matrix network 358 have designated functions which are shown in FIG. 6. The wired logic matrix 358 operates in the following manner. For example, assume the control pulse from the decoder 356 appears on lead 1 representing step No. 2 in the wired logic program, the pulse is delivered through a diode 359 and into an operational amplifier 363. The control pulse is essentially amplified and delivered over the constant lead 362 representing the numeral 2. The operational amplifier 363 is biased to a positive 5 volt DC source. FIG. 6 further shows the constant 2 being generated when the control pulse appears on lead 89 corresponding to step 89. In a similar manner, all constants 0 through 9 may be generated over the CONSTANTS bus 362 and the following functions may also be generated over the FUNCTIONS bus 366: equals, decimal point, X-squared, plus, multiplication, clear, subtraction, memory, and division. In addition, the values appearing at certain switches 18 can be accessed over SWITCHES bus 600. And finally, certain displays can be activated over DISPLAY bus 610.

In a manner to be more fully discussed, a predetermined sequence of signals appearing on the CONSTANTS bus 362, the FUNCTIONS bus 366, the SWITCHES bus 600, and the DISPLAY bus 610 can be generated by affixing a diode between the leads 0 through 89 from the decoder 356 with the leads from the aforesaid output buses. In FIG. 6, as another example, the output lead corresponding to program step 2 of the decoder 356 is not connected with a diode to the constant lead 2. Therefore, when the binary pulse appears on lead 2, no output would appear on the constant lead 2 due to the missing diode, but the pulse would activate the "division" lead where a diode is connected. In a manner also to be more fully discussed later, the CONSTANTS bus 362 from the wired logic matrix 358 representing the constants are wire-ORed to the NUMERALS bus 370. The NUMERALS bus 370 is also connected to a plurality of ten NAND-GATES 372 which will be more fully discussed later.

FIG. 7 shows the details of the calculator chip 360 with its appropriate input and output logic 372 and 374, respectively. The outputs of the wired logic sequencer 352 directly access the input circuitry 372 of the calculator chip 360. The input circuitry comprises a matrix of conventional solid state switches 376 of the type manufactured preferably by National semiconductor Corporation as CMOS 4016. The input switches 376 form a matrix that is essentially the electronic equivalent of a mechanical keyboard for a conventional hand-held calculator. In a mechanical keyboard operation, each matrix switch 376 would correspond to a mechanical pushbutton key which when pressed would connect a D output of calculator 360 to one of the three Y inputs. In the present invention, however, an electrical signal is provided to one of leads 380 which effects an electronic connection between one of the D leads and one of the Y leads. Therefore, the NUMERALS bus 370 is delivered from the wired logic sequencer 352 of FIG. 6 through the appropriate lead 380 of the corresponding solid-state switch 376 of FIG. 7. The numerals 0 through 9 labeling the solid-state switches 376 in the NUMERALS column correspond, one-for-one with the numerals 0 through 9 of the numerals bus 370. Likewise, the FUNCTIONS bus 366 from the wired logic sequencer 352 of FIG. 6 are also delivered to the appropriate leads 380 of the matrix switch 372 of FIG. 7 in the manner diagrammatically shown. It is to be noted that only certain of the matrix positions contain function control leads 380, the remaining matrix positions are not used in the present invention.

Therefore, as the decoder 356 of FIG. 6 sequentially steps the wired logic matrix through a predetermined pattern of output responses on the NUMERALS and FUNCTIONS buses, 370 and 366 respectively, such information is entered into the calculator chip 360 in the aforesaid manner through activation of selected matrix switches 376. The calculator chip 360 is conventional and is preferably manufactured by MOS Technology, Inc., Valley Forge Corporate Center, 950 Rittenhouse Road, Norristown, Pennsylvania. The Model Number is MPS 2523-002 (disclosed in SPECIFICATION FOR EIGHT FUNCTION CALCULATOR ARRAY, REV. 1-Dec. 17, 1973). In the conventional manner disclosed in the aforesaid reference, the calculator chip 360 performs certain operations dependent upon the abovesaid interconnections from the switch matrix 372.

The output of the calculator chip 360 is delivered over a seven lead bus 382 that is representative of the seven control leads for a seven-segment display. In order to use the calculator chip 360, in the present invention, certain modifications are necessary. The seven-segment information on bus 382 is inputed into a conventional read-only-memory (ROM) decoder for conversion into a four bit binary-coded-decimal (BCD) representation appearing on bus 384. The use of a ROM as a convertor is well known in the art of computer design and the present invention utilizes a conventional ROM of the type manufactured by National Semiconductor Corp. as Model No. DM76L25. In operation, the seven-segment information on bus 382 from the calculator chip 360 forms the address of a unique location in the ROM 374 whose data at that location is the BCD equivalent of the seven-segment value. The BCD information is then read out onto bus 384.

The display bus 384 is delivered into the display circuitry 20, shown in FIG. 1, to activate the various digital displays. In FIG. 8, control circuits 389 are provided for each display and operate in the following manner as discussed for the heparin display 390. The heparin display 390 comprises three seven-segment numerical displays 392. When the calculator chip 360 of FIG. 7 outputs information to the display circuitry of FIG. 8 over bus 384, the seven-segment information is delivered from the calculator chip 360 to ROM convertor 374, and into latches 394, 401, and 402. A multiplexor 400 controls the inputting of the information into the latches. The multiplexer 400 simply comprises AND-GATES 406 that are selectively activated by a high signal on the HEPARIN control lead 408 from DISPLAY bus 610 from the matrix 358. In this manner, identical control logic for PROTAMINE and BLOOD VOLUME can be activated. The UNITS latch 394 is activated by a gate-in signal appearing on the UNITS control lead of the DIGIT POSITION bus 396 coming from the D7 output lead of the calculator chip 360. The TENS digit information is outputed into the ROM convertor 374 for delivery over the display bus 384 into the TENS latch 401 under control of the gate-in signal from the TENS lead of the DIGIT POSITION bus 396 coming from the D8 output of the calculator chip 360. Likewise, in a similar manner, the hundreds information is delivered into the HUNDREDS latch 402 of the display control logic. The calculator chip 360, therefore, controls the loading of the display information, while the sequencer 352 selects which display. Once the necessary informatin has been loaded into the latch registers 394, 401 and 402 of the control logic 389, each digit position is converted in a conventional fashion from the BCD format to the seven-segment information for directly driving the display unit by a conventional converter 404.

Information can also be inputed into the calculator chip 360 from a series of external dial switches 18 as shown in FIGS. 1 and 2. The patient's height, weight, pump volume, and blood volume can be appropriately inputed into the calculator 360. In addition, the heparin and protamine parameters can be entered. All the dial switches share a common SWITCH bus 400, shown in FIG. 9, for the heparin maintenance level switches. Each position of the conventional dial switch 402 uniquely activates one of the ten leads 404 in a conventional manner. Each of the ten leads 404 has a corresponding NAND-GATE buffer 406 between it and a corresponding lead on the switch bus 400. Data appearing at the dial switch 402 is entered onto the bus 400 by signalling the appropriate gate-in lead 408 on the SWITCHES bus 600 from the matrix 358.

In a similar manner data manually entered into the dial switches for the other parameters can be selected by the sequencer 352 for inputting information into the calculator chip 360. The bus 400 inputs ten AND-GATES 400, shown in FIG. 6 and is delivered to the above-described NUMERALS bus 370 under selective activation of the READ SWITCH lead. The READ SWITCH lead is conventionally activated from the wired logic matrix 358 and it is not shown. Such activation may be performed, for example, by interconnecting one of the output leads from the decoder 356 directly to the READ SWITCH lead.

In FIG. 10, two dial swiches 402 are provided corresponding to each cell in the cell pack 12 for inputting into the system of the present invention the strength of the additive found within the chamber 40 of each cell 13. As shown, each switch 402, with its ten outputs, accesses ten AND-gates 630, each output accessing one AND-gate. The outputs of the AND-gates 630 corresponding to the UNITS switches are commonly tied with the outputs of corresponding AND-gates 630 for the remaining cells on bus 631. Likewise, the outputs of AND-gates 630 corresponding to the TENTHS switches are commonly tied on bus 633. The ten leads of UNITS bus 631 input ten AND-gates 634. Corresponding AND-gates 632 and 634 are commonly tied to SWITCH bus 400.

In operation, the first cell to coagulate signals the event over its corresponding lead in bus 250. For example assume cell No. 1 coagulates first. In FIG. 10, only those AND-gates 630 for Cell No. 1 are activated to output the manually inserted values onto buses 631 and 633. At the appropriate time interval, as will be discussed later, the wired logic sequencer 352 signals leads 600 for AND-gates 632 and 634 sequentially in order to deliver the information into the processor.

The operation of the system of the present invention will now be presented in detail by reference to FIG. 11. In the INITIALIZE state, the machine is reset to predetermined values in conventional approaches which are not necessary for the understanding and operation of this invention. Suffice it to say that the machine commences operation when cell pack 12 is inserted into the channel analyzer 14 and cover 56 is closed thereover. The sequencer 16 dependent on the positioning of toggle switch 450, shown in FIG. 2, enters one of two branches of operation. Toggle switch 450 has two states: MACHINE COMPUTE (M) or EXTERNAL PROGRAM (E). Assuming toggle switch 450 is activated in the MACHINE COMPUTE position the wired logic sequencer 352 is interconnected to interrogate the HEIGHT switches 452 by activating the appropriate lead on bus 600 from the wired logic matrix 358 and reading the height information over bus 400 and into the calculator chip 360 as previously discussed. The height of the patient has now been entered into the calculator 360.

The wired logic sequencer 352 now interrogates the status of switch 454 in order to determine the sex of the patient and to enter this information into the calculator 360. It is to be noted that whether a patient is male or female is reducible to the entry of one of two separate and distinct numerical constants. It is obvious to one skilled in the art that such a provision can be easily provided for by having the diodes 359 of the wired logic matrix 358 interconnected to appropriate CONSTANTS leads in bus 362 in series with an appropriate switch contact. For example, assume that the constant value for a male patient is 1 while that of a female patient is 3 and further assume that that information is pulsed on step 1 of the decoder. Two diodes, in the assumption, would be interconnected, one on the 1 lead and one on the 3 lead, with opposing switch contacts of switch 454 to the 1 output line of decoder 356. Depending on the status of switch 454, the appropriate diode will be switched in on the appropriate constants output lead.

The next determination in the MACHINE COMPUTE branch is to determine and enter into the calculator chip the WEIGHT from switches 456. The wired logic matrix 358 activates the appropriate switch lead on bus 600 to read out the weight information onto switch input bus 400 for delivery through gates 372 and over bus 370 into the calculator 360 by activating the appropriate solid-state switch 376.

However, if the EXTERNAL PROGRAM branch was preselected in switch 450, the BLOOD VOLUME of the patient is entered into the calculator by reading dial switches 458. The operator of the present invention therefore has the option of having the sequencer 16 determine the blood volume of the patient based on known patient physical parameters (HEIGHT, SEX, and WEIGHT) or the option of manually entering in an estimated blood volume. The state of the perfusion art is such that vast majority of patients fall within known classes of body proportions and sizes having quantitatively determined norms of blood volume. However, patients of unusual proportions, such as babies, thin persons, fat persons, and dwarfs have blood volumes that do not fall within expected norms. In such cases, the operator of the present invention would estimate the blood volume and enter that value by flicking the EXTERNAL PROGRAM switch.

The wired logic sequencer 352 is now ready to analyze the status of switch 460. Switch 460 has two possible states: ANALYZE (A) or NEUTRALIZE (N). In the ANALYZE branch, the information residing in the PUMP VOLUME dial switches 462 are entered into the calculator chip 360 in the manner previously discussed for the other switches. In the ANALYZE mode, the patient is usually in surgery and he is interconnected into an extracorporeal circuit wherein additional blood has been added to the patient's blood. The amount of that additional blood is termed the PUMP VOLUME. Therefore, the ANALYZE branch adds the PUMP VOLUME to the previously determined blood volume of the patient to display in display 464 the total blood volume of the patient. If, however, the NEUTRALIZE mode was selected corresponding to the situation prior to surgery or after surgery, the patient is not interconnected with the extra-corporeal circuit and therefore the blood volume determined previously would correspond to the blood volume in consideration and would be displayed in display 464. Of course, if the patient is not interconnected into an extracorporeal circuit then the value entered in the switches 462 would be zero.

The next sequence of operation in the wired logic sequencer 352 is to determine the status of switch 466, that is: MAINTENANCE or TOTALIZE. When switch 466 is activated in the MAINTENANCE mode, the wired logic matrix 358 interrogates the heparin level switches 468 to input into the calculator chip 360, in the above-described manner, the heparin maintenance information found in switches 468. This information is determined by the present invention prior to surgery. In other words, the present invention determines the amount of heparin to be added to the patient's blood prior to surgery and displays the value in the HEPARIN display. During surgery, however, this displayed information is manually recorded by setting the heparin LEVEL switches 468. During surgery, it is mandatory that the heparin be maintained at that predetermined level by periodic injections of additional heparin to overcome the effect of heparin half-life. Therefore, when switch 466 resides in the MAINTENANCE mode, the maintenance LEVEL information in switches 468 is entered into the calculator 360. However, if the switch 466 is in the TOTALIZE mode, then the maintenance LEVEL information in switches 468 is bypassed.

In the next operation, the wired logic matrix 358 now determines the protamine LEVEL from switches 402 of the particular test cell that was the first to coagulate as previously discussed for FIG. 10. The strength of the protamine necessary to neutralize the heparin concentration in the test cell coagulating first is entered into the calculator chip 360. As previously discussed, the amount of protamine required to cause the first test cell to coagulate is indicative of the strength of heparin within the blood sample. Therefore, knowledge of the strength of protamine to effectively neutralize all heparin within the blood is used to determine the actual amount of heparin in the patient's blood. The wired logic sequencer 352 displays this calculated value of heparin in display 470. Since protamine and heparin can be acquired from various sources of varying concentrations, the ratio of protamine to heparin is desired. These are known conventional values and are conventional in the state of the art. Generally the ratio varies between 1.0 and 1.4 (i.e. 1.4 mm of protamine to 100 units of heparin). This value is manually set in switches 472 for a given brand of commercial protamine and the wired logic sequencer 352 after displaying the heparin concentration in the blood enters this information into the calculator chip 360 in order to calculate the amount of protamine necessary to neutralize the heparin. That value is then displayed in display 474. At the completion of the protamine display, the wired logic sequencer recycles to the beginning of the program.

Prior to surgery, the machine would be initially set as follows. Switch 450 is set to either MACHINE COMPUTE or EXTERNAL PROGRAM, depending on the physical parameters of the patient. The switch 460 is set to NEUTRALIZE and switch 466 is set to TOTALIZE. As previously discussed, the wired logic sequencer 352 then calculates and displays the blood volume 464, and calculates and displays the amount of heparin 470 to be added to the patient's blood to heparinize the patient.

During surgery, the present invention would have the following parameters set. The maintenance level switches 468 is set to the value calculated above in the TOTALIZE Mode for heparinizing the patient. The switch 450 is set as above and would use the same parameters for height, weight, sex and blood volume. Switch is set to ANALYZE and the PUMP VOLUME of the extracorporeal circuit would be entered into switches 462. Switch 466 is set in the MAINTENANCE mode. The machine calculates and displays the blood volume 464 and the amount of heparin 470 required to correct any half-life decay or the amount of protamine 474 necessary to counteract any surplus heparin above the maintenance level.

After surgery, to totally neutralize the heparin in the patient or, later, in the rebound conditions, switch 450 is maintained, as before. Switch 460 is set in the NEUTRALIZE mode and switch 466 is set in the TOTALIZE mode. The wired logic sequencer 352 displays the new blood volume 464 and the amount of protamine 474 to be added to neutralize the amount of heparin 470 measured in the blood.

While the preferred embodiment discloses use of a wired logic matrix and calculator chip, it is to be understood that such disclosure is not intended to limit or delimit the novel features of the present invention. In fact, the present invention may utilize any of a number of conventional control arrangement including a microprocessor control. In addition, the actual mathematical relationships for determining the amount of anticoagulant and additive to be injected have not been presented. These mathematical relationships are quantitively determined from studying the reactions to classes of similar patients. Such relationships are, therefore, subject to refinement and are dependent on the type of drug used. The system of the present invention may be adapted to use any refined control relationship by one skilled in the art.

While certain illustrative embodiments of the present invention have been shown in the drawings and described above in considerable detail, it should be understood that there is no intention to limit the invention to the specific form disclosed. On the contrary, the intention is to cover all modification, alternative constructions, equivalents and uses folowing within the spirit and scope of the invention as expressed in the appended claims.

We claim:

1. A system for determining the coagulation time for blood and components thereof, said system comprising:
    a timer,
    means holding said blood, means for promoting the acceleration of coagulation of said blood in said holding means,
    means cooperative with said promoting means for signalling the separation of coagulated blood from non-coagulated blood
    means operative upon the acceleration of coagulation by said promoting means for starting said timer, and
    means responsive to a signal from said signalling means for stopping said timer, said stopped timer being indicative of the total time elapsed for coagulation of said blood.

2. The system of claim 1 in which said timer comprises:
    an oscillator for generating a series of timing pulses,
    a counter responsive to the operation of said starting means for counting said timing pulses, said counter being further responsive to a signal from said stopping means for stopping the counting of said pulses, and
    a. display operative with said counter for displaying said coagulation time when said counter is stopped.

3. A system for determining the coagulation time for blood and components thereof, said system comprising:
    a timer,
    means for holding said blood,
    means operatively engaging said holding means for injecting gas into said blood, said injected gas causing a plurality of bubbles transporting some of said blood above the surface of said blood, means connected to said holding means above the surface of said blood for collecting said transported blood only when coagulation of said blood occurs, said surface of said blood dropping when said collection of said transported blood occurs, means responsive to the injection of said gas for starting said timer, means responsive to said surface drop for generating a signal, said signal being indicative of the event of coagulation, and means responsive to said signal for stopping said timer, said stopped timer being indicative of the total time elapsed for coagulation of said blood.

4. The system of claim 3 in which said injecting means comprises:
a motor,
a pump operative by said motor for generating a constant supply of gas, and
a nozzle cooperative with said pump for injecting gas into said blood.

5. The system of claim 3 further comprising means for activating said generating means only after a predetermined time so that said bubbles are able to fully form above said surface of said blood.

6. The system of claim 3 in which said generating means comprises:
means responsive to said surface of said blood dropping for effectuating an electrical signal, and
means responsive of said signal for extending said signal to said timer.

7. The system of claim 6 in which said effectuating means comprises:
a light source for directing a beam of light through said blood in said holding means, said beam being directed through said blood below said surface, and
a photocell opposing said light source and receptive of said light beam for generating a first signal when said blood drops below the path of said beam due to said collection.

8. The system of claim 3 further comprising means operative upon the lack of gas flow after said engagement for emitting a warning signal.

9. The system of claim 8 in which said emitting means comprises:
a light source for directing a beam of light through said bubbles above said surface of said blood in said holding means,
a photocell opposing said light source and receptive of said light beam for generating a signal only when bubbles are not formed above said surface of said blood, and
a lamp operative upon receipt of said signal for flashing a warning condition.

10. The system of claim 8 further comprising means for activating said emitting means only after a predetermined time so that said bubbles are able to fully form above the surface of said blood.

11. A system for determining the coagulation time for anticoagulated blood after neutralizing the anticoagulant in said blood with an additive, said system comprising:
a timer,
first means for holding said blood,
second means for holding said additive,
means cooperative with said first and second holding means for injecting gas and said additive into said blood, said injected gas causing a plurality of bubbles transporting some of said blood to form above the surface of said blood,
means operative with said injection for starting said timer,
means connected to said holding means above the said surface of said blood for collecting said bubbles only when coagulation of said blood occurs, and
means operative upon said collection for stopping said timer.

12. The system of claim 11 in which said timer comprises:
an oscillator for generating a series of timing pulses,
a counter responsive to a signal for said starting means for counting said timing pulses, said counter being further responsive to a signal from said stopping means for stopping the counting of said pulses, and
a display operative with said counter for displaying said coagulation time when said counter is stopped.

13. The system of claim 11 in which said injecting means comprises:
a motor,
a pump operative by said motor for generating a constant supply of gas, and
a nozzle coperative with said pump for injecting gas into said blood in said holding means.

14. The system of claim 11 further comprising means connected to said generating means for activating said generating means only after a predetermined time so that said blood bubbles are able to fully develop above said surface of said blood.

15. The system of claim 11 in which said stopping means comprises:
means responsive to said surface of said blood dropping for generating an electrical signal, and
means responsive of said signal for amplifying said signal and extending said amplified signal to said timer.

16. The system of claim 15 in which said generating means comprises:
a light source for directing a beam of light through said blood in said holding means, said beam being directed through said blood below said surface, and
a photocell opposing said light source and receptive of said light beam for generating a first signal when said blood drops below the path of said beam due to said collection.

17. The system of claim 11 further comprising means operative upon the lack of gas flow after said engagement for generating a warning signal.

18. The system of claim 17 in which said generating means comprises:
a light source for directing a beam of light through said bubbles above said surface of said blood in said housing means,
a photocell opposing said light source and receptive of said light beam for generating a signal only when bubbles are not formed above said surface of said blood,
a lamp operative upon receipt of said sign for flashing a warning condition, and
means responsive to said signal for amplifying said signal and extending said signal to said lamp.

19. The system of claim 17 further comprising means connected to said generating means for activating said generating means only after a predetermined time so that said bubbles are able to fully develop above the surface of said blood.

20. A system for determining the coagulation time of the first of a plurality of blood specimens to coagulate, said system comprising:
   a plurality of cells for holding said blood specimens, one of said blood specimens being placed in one of said cells,
   a pack for containing said plurality of cells,
   a plurality of detectors operatively engaging said pack for sensing the event of blood coagulation, one of said detectors being cooperative with one of said cells for sensing coagulation of the blood specimen in the aforesaid cell,
   a timer,
   means operative upon said engagement of said detectors with said pack for starting said timer,
   means operative upon only the first detector to sense coagulation of the blood specimen in its corresponding cell for stopping said timer, said stopped timer being indicative of the total elapsed time for coagulation of said blood specimen in said aforesaid cell, and
   means responsive to stopped timer for identifying aforesaid cell.

21. The system of claim 20 wherein each of said detector comprises:
   means operatively engaging said cell in said pack for injecting gas into said specimen disposed with said cell, said injected gas causing a plurality of bubbles transporting some of said blood to form above the surface of said specimen,
   means in said cell above the surface of said blood specimen for collecting the transported blood in said blood bubbles only when coagulation of said blood occurs, said surface of said blood dropping when said collection occurs,
   means responsive to said surface of said specimen dropping for generating an electrical signal, and
   means responsive of said signal for amplifying said signal and extending said signal to said stopping means.

22. The system of claim 21 further comprising means connected to each of said detectors for activating said detectors only after a predetermined time so that said bubbles are able to fully develop above said surface.

23. The system of claim 21 further comprising a plurality of gas flow sensors operatively engaging said pack for detecting the flow of said gas, one of said sensors being cooperative with one of said cells for sensing the flow of gas in the aforesaid cell.

24. A system for determining the amount of anticoagulant or neutralizing additive to be injected into a patient's blood so that the anticoagulant in said blood is maintained at a desired level, said system comprising:
   means operative on a plurality of samples of said blood for measuring the amount of anticoagulant present within said blood, and
   means responsive to said measurement for determining the amount of anticoagulant to be injected into said patient when said measured level is less than said desired level, said determining means being further capable of determining the amount of neutralizing additive to be injected into said patient when said measured level is greater than said desired level.

25. The system of claim 24 wherein said measuring means comprises:
   a plurality of cells, each of said cells containing a sample of said blood and a predetermined amount of said additive, said additive being of different concentrations in different cells,
   first means for storing the additive concentration information for each of said plurality of cells in relation to the identity of the cell,
   means for generating a signal when the first of said cells coagulates, said signal uniquely identifying said cell, and
   means operative upon the receipt of said signal for delivering the additive concentration information corresponding to said cell from said storing means to said delivery means.

26. The system of claim 24 further comprising:
   means responsive to a determination of the amount of said anticoagulant to be injected for displaying the aforesaid amount, and
   means responsive to a determination of the amount of said additive to be injected for displaying the aforesaid amount.

27. The system of claim 25 wherein said means for storing comprise a plurality of switches.

28. The system of claim 25 wherein said determining means further comprises:
   second means for storing patient information,
   third means for storing said desired level of anticoagulant,
   means responsive to said measurement for selectively reading information from said first, second, and third storing means,
   means operative upon said measurement for controlling said selective reading of said first, second, and third storing, and
   means cooperative with said controlling means and receptive of said selected information read from said first, second and third storing means for calculating the amount of said anticoagulant or additive to be injected.

29. A system for determining the amount of anticoagulant or neutralizing additive to be injected into a patient's blood so that said anticoagulant in said blood is maintained at a desired level, said system comprising:
   a plurality of cells, each of said cells containing a sample of said blood and a predetermined amount of said additive, said additive being of different concentrations in different cells,
   first means responsive to a manual input for storing information, said first storing means containing the additive concentration values for each of said plurality of cells in relation to the identify of the cell,
   second means responsive to a manual input for storing information, said second storing means containing physical parameters unique to said patient,
   third means responsive to a manual input for storing information relating to said desired level of anticoagulant,
   means responsive to the insertion of said cells into the system for generating a signal when the first of said cells coagulates, said signal uniquely identifying said cell,
   means responsive to said signal for selectively reading information from said first, second, and third storing means,
   means operative upon said signal for controlling said selective reading of said first, second, and third storing means, and means cooperative with said controlling means and receptive of said selected information read from said first, second, and third storing means for calculating the amount of anticoagulant to be injected into said patient when said measured level is less than said desired level and for calculating the amount of neutralizing additive to be injected into said patient when said measured level is greater than said desired level.

30. The system of claim 29 further comprising:
means responsive to a calculation of the amount of said anticoagulant to be injected for displaying the aforesaid amount, and
means responsive to a calculation of the amount of said additive to be injected for displaying the aforesaid amount.

31. The system of claim 29 in which said second storing means comprises:
means for entering and storing the height of said patient,
means for entering and storing the weight of said patient,
means for entering and storing the sex of said patient, and
means for entering and storing the pump volume of said patient in the event said patient is interconnected with an extracorporeal circuit.

32. The system of claim 29 further comprising means responsive to said signal for displaying the identity of said cell.

33. The system of claim 29 in which said calculating means further comprises means responsive to said selectively read patient information for determining said desired level of anticoagulant.

34. The system of claim 33 further comprising means responsive to a determination of the amount of said desired level for displaying the aforesaid amount.

35. The system of claim 29 further comprising means responsive to said insertion and said signal for determining the elapsed time for coagulation of said blood in said cell.

36. The system of claim 35 further comprising means responsive to said elapsed time determination for displaying the aforesaid amount.

37. The system of claim 29 in which said calculating means further comprises means responsive to said selectively read patient information for determining the blood volume of said patient.

38. The system of claim 37 further comprising means responsive to said blood volume determination for displaying the aforesaid amount.

39. A method for determining the amount of anticoagulant or neutralizing additive to be injected into the blood of a patient so that said blood is maintained at a desired level of anticoagulant, said method comprising the steps of:
taking samples of the patient's blood,
mixing predetermined amounts of varying concentrations of the neutralizing additive into each of the samples,
storing the concentration information of the additive in relation to the identity of each sample,
signalling the identity of the sample which is the first to coagulate,
reading the stored concentration information for the first sample to coagulate in response to said identify signal,
determining the amount of anticoagulant with the blood in response to the reading of the concentration information of the additive within the first sample to coagulate, and
determining the amount of desired anticoagulant to be injected in response to the determination of the amount of anticoagulant already in the blood.

40. The method of claim 39 comprising the additional steps of:
injecting gas into each sample in response to the mixing of the additive into the sample, and
displaying the elapsed time for coagulation in response to said identity signal.

41. The method of claim 39 in which the step of signalling further comprises the steps of:
injecting gas into each sample in response to the mixing of the additive into the sample,
collecting the blood transported by bubbles formed by the injected gas above the surface of the sample only when the blood coagulates, and
generating a signal in response to the collection of the transported coagulated blood.

42. The method of claim 39 in which the step of determining the amount of anticoagulant comprises the steps of:
storing information relating to the physical characteristics of the patient,
determining the blood volume of the patient based on the stored patient information,
displaying the blood volume of the patient in response to the blood volume determination, and
calculating the amount of anticoagulant to be injected to maintain the desired level of anticoagulant in response to the amount of anticoagulant in the blood and the blood volume of the patient.

43. The method of claim 39 in which the step of determining the amount of anticoagulant comprises the steps of:
storing information relating to the blood volume of the patient,
determining the blood volume of the patient based on the aforesaid stored information,
displaying the blood volume of the patient in response to the blood volume determination, and
calculating the amount of anticoagulant to be injected to maintain the desired level of anticoagulant in the blood and the blood volume of the patient.

* * * * *